US011890312B2

(12) United States Patent
Magon

(10) Patent No.: US 11,890,312 B2
(45) Date of Patent: Feb. 6, 2024

(54) COMPOSITION COMPRISING HERBAL EXTRACTS

(71) Applicant: Pimago Ltd., Tel Aviv (IL)

(72) Inventor: Eran Magon, Tel Aviv (IL)

(*) Notice: Subject to any disclaimer, the term of this patent is extended or adjusted under 35 U.S.C. 154(b) by 303 days.

(21) Appl. No.: 17/286,499

(22) PCT Filed: Oct. 10, 2019

(86) PCT No.: PCT/IL2019/051112
§ 371 (c)(1),
(2) Date: Apr. 19, 2021

(87) PCT Pub. No.: WO2020/079682
PCT Pub. Date: Apr. 23, 2020

(65) Prior Publication Data
US 2021/0346450 A1    Nov. 11, 2021

Related U.S. Application Data

(60) Provisional application No. 62/747,152, filed on Oct. 18, 2018.

(51) Int. Cl.
| *A61K 36/00* | (2006.01) |
| *A61K 36/48* | (2006.01) |
| *A23L 33/105* | (2016.01) |
| *A61P 17/06* | (2006.01) |
| *A61K 36/24* | (2006.01) |
| *A61K 36/61* | (2006.01) |
| *A61K 45/06* | (2006.01) |
| *A61K 36/58* | (2006.01) |

(52) U.S. Cl.
CPC .......... *A61K 36/48* (2013.01); *A23L 33/105* (2016.08); *A61K 36/24* (2013.01); *A61K 36/61* (2013.01); *A61K 45/06* (2013.01); *A61P 17/06* (2018.01); *A61K 36/58* (2013.01)

(58) Field of Classification Search
CPC ...................................................... A61P 17/06
See application file for complete search history.

(56) References Cited

U.S. PATENT DOCUMENTS

| 5,693,327 | A | * | 12/1997 | Shah | ............. | A61K 36/185 |
| | | | | | | 424/734 |
| 9,233,133 | B2 | | 1/2016 | Chaudhary | | |
| 2015/0297652 | A1 | | 10/2015 | Balaraman | | |
| 2018/0318374 | A1 | | 11/2018 | Shetty | | |

FOREIGN PATENT DOCUMENTS

| GB | 2274058 A | 7/1994 |
| IN | 2006CH01387 A * | 9/2008 |
| IN | MUM200702469 | 7/2009 |
| IN | DEL201102027 | 1/2013 |
| IN | MUM201404051 | 6/2016 |

OTHER PUBLICATIONS

Mishra N. P. et al. Journal of Global Biosciences 2014, 3, 731-734.
Ferdous T. et al. "Management of Psoriasis by Saribadyarista: A Case Study" Int. J. Ayu. Pharm. Chem. 2016, 5, 92-103.
Das S. et al. "The Bioactive and Therapeutic Potential of *Hemidesmus indicus* R. Br. (Indian Sarsaparilla) Root" Phytother. Res. 2013, 27, 791-801.
Krishnaveni M. et al. J. Basic. Clin. Physiol. Pharmacol. 2010, 21, 3-105.
Deb et al. J. Pharm. Phyt. 2016, 5, 194-197.
Bag et al. Asian Pac J Trop Biomed 2013, 3, 244-252.
Dhama et. al Rec. Pat. End. Metab. Immun. Drug Discovery 2016, 10, 96-111.
PCT Search Report for International Application No. PCT/IL2019/051112, dated Feb. 6, 2020 ; 3 pp.
PCT Written Opinion for International Application No. PCT/IL2019/051112, dated Feb. 6, 2020; 5 pp.
PCT Preliminary Report for International Application No. PCT/IL2019/051112, dated Apr. 14, 2021; 6 pp.
Foundation for Revitalisation of Local Health Traditions (FRLHT) (2002). A Report on Simple forulations for primary health care uses based on Ayurveda for Commercially Important plant Species of *Andhra Pradesh*. available online at: http://forest.ap.nic.in/JFM%20CFM/CFM/Special20Reports/FRLHT/Reports/14.%20tsm.pdf.
TKDL Database, Traditional Knowledge Resource: Database accession No. SL/440 (abstract). Title: Khadirastakakvathah, Knowledge known since: 50 years, 4pp.
TKDL Database, Traditional Knowledge Resource: Database accession No. SG/161B (abstract). Title: Tvak Vikar, Knowledge known since: 1000 years, 3pp.
TKDL Database, Traditional Knowledge Resource: Database accession No. AH5/3470A (abstract), Title: Mazmaza Bara-e-Qulaa Baarid, Knowledge known since: 100 years, 3pp.
TKDL Database, Traditional Knowledge Resource: Database accession No. VS/2762 (abstract), Title: Guducydikasayah, Knowledge known since: 50 years, 3pp.
TKDL Database, Traditional Knowledge Resource: Database accession No. HG/615 (abstract), Sahacaradikvathah, Knowledge known since: 200 years, 3pp.
TKDL Database, Traditional Knowledge Resource: Database accession No. JA6/973A52 (abstract), Title: Dawa Bara-e-Hikka, Knowledge known since: 100 years, 3pp.
TKDL Database, Traditional Knowledge Resource: Database accession No. JA6/133 (abstract), Title: Ushba, Knowledge known since 100 years, 4pp.
Extended European Search Report for European Patent Application No. 19873131.7, dated Jul. 29, 2022, 9pp.

* cited by examiner

*Primary Examiner* — Qiuwen Mi
(74) *Attorney, Agent, or Firm* — The Roy Gross Law Firm, LLC; Roy Gross

(57) ABSTRACT

A composition for treating skin disorders including a mixture of herbal extracts of *Azadirachta indica, Acacia catechu, Hemidesmus indicus, Phyllanthus emblica, Terminalia bellirica, Terminalia chebula* and optionally *Tinospora cordifolia* and use thereof. A method for treating skin disorders using the composition is also disclosed.

16 Claims, No Drawings

COMPOSITION COMPRISING HERBAL EXTRACTS

This application is a National Phase of PCT Patent Application No. PCT/IL2019/051112 having International filing date of Oct. 10, 2019, which claims the benefit of priority of U.S. Provisional Patent Application No. 62/747,152, filed Oct. 18, 2018, the contents of which are all incorporated herein by reference in their entirety.

TECHNICAL FIELD OF THE INVENTION

The present invention relates to medicinal, nutraceutical, dietary supplements and food additive compositions. In particular it relates to compositions comprising herbal extracts for treating skin disorders, specifically psoriasis.

BACKGROUND

*Azadirachta indica*, also referred to as Neem, is traditionally regarded as providing relief from many diseases, and used for thousands of years in Indian and African continents. Different parts of the plant including flowers, leaves, seeds and bark have been used to treat both acute and chronic human diseases and used as an insecticidal, antimicrobial, larvicidal, antimalarial, antibacterial, antiviral, and spermicidal agent.

*Acacia catechu* (sin. *Black catechu*) has been used as an antimicrobial, anti-inflammatory and antifungal agent, coagulant, vermifuge, antidiarrheal, and astringent, and has also been employed to heal wounds, treat obesity and diabetes, and maintain oral hygiene.

The root of *Hemidesmus indicus* R. Br., commonly known as Indian Sarsaparilla, is used traditionally to treat a wide variety of illnesses including rheumatism, leprosy, impotence, urinary tract and skin infections. The anticancer, antioxidant, anti-inflammatory, antipyretic, analgesic, antimicrobial, antidiabetic, hepatoprotective, cardioprotective, renoprotective, neuroprotective and immunomodulatory properties of *H. indicus* have been investigated in numerous in vivo and in vitro studies. Among these, its antioxidant and antimicrobial activity was well documented. The phytochemistry and therapeutic applications of *H. indicus* root is detailed in Das S. et al. *Phytotherapy Res.* 27, 2013, 791-801.

*Phyllanthus emblica* (syn. *Emblica officinalis*), commonly known as Indian gooseberry or Amla, family Euphorbiaceae, is an important herbal drug used in Unani (traditional Greek—Arab medicine) and Ayurvedic (traditional indian medicine) systems of medicine. The plant is used both as a medicine and as a tonic to build up lost vitality and vigor. *Phyllanthus emblica* is highly nutritious and could be an important dietary source of vitamin C, amino acids, and minerals. The plant also contains phenolic compounds, tannins, phyllembelic acid, phyllembelin, rutin, curcuminoids, and emblicol. All parts of the plant are used for medicinal purposes, especially the fruit, which has been used in Ayurveda as a potent "Rasayana"—a rejuvenate potent antioxidant agent, and in traditional medicine for the treatment of diarrhea, jaundice, and inflammation. See Krishnaveni M et al. *J. Basic. Clin. Physiol. Pharmacol.* 2010, 21, 3-105

Various plant parts show antidiabetic, hypolipidemic, antibacterial, antioxidant, antiulcerogenic, hepatoprotective, gastroprotective, and chemopreventive properties.

*Terminalia bellirica*—is a medicinal plant used for the treatment of various ailments in the traditional system of medicine such as Ayurveda where it has been prescribed as a rejuvenator and general health tonic, and acts as an antioxidant, antimicrobial, antidiarrheal, anticancer, antihypertensive, hepatoprotective & antipyretic agent. The fruit of the plant is one of the components of the age old ayurvedic composition—"Triphala" (a combination of *Phyllanthus emblica, Terminalia bellirica* and *Terminalia chebula*). See Deb A. et al. *J. Pharmacog. Phytochem.* 2016, 5, 194-197.

*Terminalia chebula* possesses high medicinal value and is traditionally used for the treatment of various ailments for human beings. Some of the folklore people used this plant in the treatment of asthma, sore throat, vomiting, hiccough, diarrhea, dysentery, bleeding piles, ulcers, gout, heart and bladder diseases. The plant has been demonstrated to possess multiple pharmacological and medicinal activities, such as antioxidant, antimicrobial, antidiabetic, hepatoprotective, anti-inflammatory, antimutagenic, antiproliferative, radioprotective, cardioprotective, antiarthritic, anticaries, gastrointestinal motility and wound healing activity. See Bag A. et al. *Asian Pac. J. Trop. Biomed.* 2013, 3, 244-252.

*Tinospora cordifolia*—The *Tinospora* species are a group of important medicinal plants used in the ethnomedical treatment of colds, headaches, pharyngitis, fever, diarrhea, oral ulcer, diabetes, digestive disorder, and rheumatoid arthritis. The medicinal applications of *Tinospora cordifolia* is in countering various disorders and used as an antioxidant, antihyperlipidemic, hepatoprotective, cardiovascular protective, neuroprotective, osteoprotective, radioprotective, anti-anxiety, adaptogenic agent, analgesic, anti-inflammatory, antipyretic, a thrombolytic agent, antimicrobial, immunomodulator and anti-cancer agent. The plant is also a source of micronutrients viz. copper, calcium, phosphorus, iron, zinc and manganese. See Dhama, K. et al. Rec. *Pat. End. Metab. & Immun. Drug Discovery* 2016, 10, 96-111.

Psoriasis is a chronic, autoimmune, inflammatory, and non-contagious disease. Despite causing great suffering, physical and mental and even a social rejection, the disease is incurable and available solutions provide only temporary relief.

It is estimated that 3% of the world population, approximately 150 million people, suffer from psoriasis. In Western Europe alone, there are 60 million known cases of the disease. In the USA—7 million.

We live in an era where the trend is "back to nature"— natural treatments are highly desired and wanted. Many medical doctors use complementary medicines and the treatments are in part sponsored by the medical establishment (through the alternative medicine's departments in hospitals and in the health maintenance organization, HMO). Therefore, a natural solution, effective and inexpensive for psoriasis disease (as well as other skin disorders) will be well accepted and desired worldwide.

Compositions for treating skin disorders which comprise extracts of herbs described above are known.

A commercial product, namely Neem Guard™ comprising 350 mg Neem (*Azadirachta indica*), 75 mg Giloy (*Tinospora cordifolia*) and 75 mg Triphala is claimed to treat acne and to exhibit cosmetic, antifungal and antibacterial properties.

India Patent Application Publication No. 04051/MUMNP/2014 discloses an oral medicinal composition for treating acne and other skin disease including psoriasis comprising *Azadirachta indica, Acacia catechu, Hemidesmus indicus, Rubia cordifolia, Glycyrrhiza glabra, Tinospora cordifolia, Solanum nigrum*, and at least one pharmaceutically acceptable excipient.

U.S. Pat. No. 9,233,133 discloses a herbal composition for blood purification, blood detoxification and in the treatment and management of disorders related to accumulation of toxins in the body including skin diseases and psoriasis, comprising as an active ingredient one or more herb selected from a group of extracts including *Accacia catachu*, *Hemidesmus indicus* and one or more bio-availability enhancer both taken in a specific therapeutically active amount.

US Patent Application Publication No. 2015/0297652 teaches a composition comprising at least one of *Albizia lebbeck, Sophora flavescens, Hibiscus rosa sinensis, Phyllanthus emblica* (syn. *Emblica officinalis*), *Azadirachta indica, Centella asiatica, Ganoderma, Rubia cordifolia, Scutellaria baicalensis, Astragalus membranaceus, Ocimum tenuiflorum* (syn. *Ocimum* sanctum) Acorns, *Artemisia, Rheum, Schisandra* and *Ophiopogon japonicas* and their use in preventing, treating, alleviating symptoms and/or mitigating skin disorders and/or disease. *Hemidesmus indicus, Terminala chebula, Terminalia bellirica* and *Tinospora cordifolia* are mentioned among many others as additional ingredients to the aforementioned composition for specific uses.

Psoriasis is not explicitly mentioned as one of the target skin disorders to be treated by this composition.

*Acacia catechu* has scientifically proven anti-inflammatory qualities and is traditionally used for treating skin diseases and as an astringent.

In an ethno-botanical study by Mishra et al. (*Journal of Global Biosciences* 2014, 3, 731-734) described 35 herbs traditionally used to treat skin diseases by tribes in central India, including *Azadiracta indica* and *Hemidesmus indicus*.

A case study by Hossain (*Int. J. Ayu Pharm. Chem.* 2016, 5, 92-103) disclosed the use of Saribadyarista, a traditional herbal formula, for blood detoxification used to treat one psoriasis patient. The formula contains 71 (!) herbs and other plants extracts, in a liquid preparation, including *Hemidesmus indicus, Azadirachta indica, Tinospora cordifolia, Emblica officinalis, Terminalia chebula, Acacia catechu*. In this single case report the Saribadyarista was given in a dose of 60-90 ml per day for one year, which means, about 2.5 liters per month. Such a dose is impractical and it is uncommercial to prescribe to a patient such a huge amount of herbal medicine each month for one year.

It may also lead to a compliance problem.

SUMMARY OF THE INVENTION

The object of the invention is to provide a composition for treating skin disorders, in particular psoriasis.

A further object of the invention is to provide an herbal composition for treating psoriasis, in particular, a formula composed of medicinal herbs from the field of Ayurveda.

A further object of the invention is to provide a natural remedy formula which neither uses synthetic chemicals as active ingredients A further object of the invention is to provide a natural remedy formula free of taste enhancers.

A further object of the invention is to provide an oral formula which being feasible and manageable for oral administration with high patient compliance.

A further object of the invention is to provide a cure for psoriasis without recurrence.

A further object of the invention is to provide a method for treating skin disorders including psoriasis having high patient compliance and minimal and even no recurrence.

According to a first aspect, the invention provides an oral composition for treating skin disorders comprising a mixture of herbal extracts comprising extracts of *Azadirachta indica, Acacia catechu, Hemidesmus indicus, Phyllanthus emblica, Terminalia bellirica* and *Terminalia chebula*.

The composition of the invention may further comprises *Tinospora cordifolia*.

The concentrations of the herbal extracts in the mixture of herbal extracts can be in the ranges 24-48 W/W % *Azadirachta indica*, 24-44 W/W % *Acacia catechu* (sin. Black catechu), 20-44 W/W % *Hemidesmus indicus* R. Br., 4-5 W/W % *Phyllanthus emblica*, 4-5 W/W % *Terminalia bellirica*, and 4-5 W/W % *Terminalia chebula*, out of the total weight of the dry mixture.

The composition described above can be used for treating a skin disorder selected from: psoriasis, psoriatic arthritis, acne, aphthous stomatitis, gingivitis, pemphigus vulgaris, urticaria, dermatitis including seborrheic dermatitis, atopic dermatitis, dermatoses and eczema.

The composition described above can be used in detoxifying treatments.

The composition described above can be used as liver detoxifying agent.

The composition described above may be formulated as a capsule, a suspension, a tablet a chewable tablet, a lozenge, syrup, paste, mouth spray or a nose spray.

The composition described above further comprises an antacid.

According to another aspect, the invention provides a use of a composition as described above for treating a skin disorder selected from: psoriasis, psoriatic arthritis, acne, aphthous stomatitis, gingivitis, pemphigus vulgaris, urticaria, dermatitis including seborrheic dermatitis, atopic dermatitis, dermatoses and eczema.

According to another aspect, the invention provides a method for treating a skin disorder selected from: psoriasis, psoriatic arthritis, acne, aphthous stomatitis, gingivitis, pemphigus vulgaris, urticaria, dermatitis including seborrheic dermatitis, atopic dermatitis, dermatoses and eczema comprising administering the composition defined above to a patient in need.

Advantages of the Invention

The method of treatment according to the invention provides a simple treatment to psoriasis and other skin autoimmune diseases such as psoriasis, psoriatic arthritis, acne, aphthous stomatitis, gingivitis, pemphigus vulgaris, urticaria, dermatitis including seborrheic dermatitis, atopic dermatitis, dermatoses and eczema which only involves the oral uptake of the herbal composition according to the invention, twice or three times a day. It does not require time consuming dermal application of pastes or UV radiations treatments.

The method of treatment and the composition according to the invention provide a solution for the patient dependence in repeated visits in a clinic or a medical center; a fast and dramatic improvement with an average improvement of about 85% in 4-6 weeks; a natural—herbal medicine which is in line with the "back to nature", and health awareness trends; has no adverse side-effects, is inexpensive, and provide excellent patient compliance.

The composition of the of the invention, as well as the method of treatment and use if the composition bare many advantages over the known products and currently available treatments which are summarized herein below.

A simple treatment—an oral dosage intake of an herbal capsule to be administered twice daily. In some embodiments, especially with patients that initially did not respond to the treatment—three times a day.

No need for any pastes or ointments—no need of rubbing anything on the skin, an action that weighs heavily on daily functioning.

The treatment is very easy to apply—one known problem in treating psoriasis and any other difficult to treat disease is the compliance of the patient to continue with the treatment. The simplicity of treatment of the invention mitigates the compliance issue. The composition can be taken any time, regardless of diet.

No dietary changes—there is no compulsory prior demand for dietary changes. Nonetheless, reducing consumption of coffee, alcohol, vinegar, fried food, oranges and orange juice, increases the effect of the treatment.

No disturbance of the patient's daily life—there is absolutely no need for continuing visits to any clinic or health centers.

The improvements are fast and dramatic—most patients improved drastically during the first 3-4 weeks.

The treatment is natural—the composition of the invention is based on safe plants that are in use for thousands of years with no known side effects.

Green solution—the composition's active ingredients are all-natural ingredients. In this era of "back to nature", organic food and health awareness—this can be a preferable solution for thousands of patients who prefer a more natural solution for their disease.

It is an inexpensive and low cost product—herbal extracts are generally low cost products.

Good compliance: as this treatment is so much easier for the patient comparing to the other psoriasis treatments available, and as it gives good and quick results without any suffering, the patient will co-operate gladly with it, and so we can make many people less miserable.

Cost effective treatment: the treatment does not involve time-consuming procedures such as going to specific clinics for phototherapy, hospitalization, expensive medications, and no absence from work and waste of economic resources.

No age limitation: the herbal capsules can be taken in any age.

There is no restriction on a particular population: the herbal capsules can be given during pregnancy, or for patients with skin sensitivity to sunlight. It can be used by people with history of skin tumors, history of cancerous tumors, kidney or liver dysfunctions, cataract and heart diseases.

No side effects were noticed during and after the use of the herbal capsules such as—skin itching, Melanoma and non-Melanoma skin cancer and genital skin cancer.

Reducing social resection and shame: improving and curing the psoriasis skin lesions improve also the tremendous emotional suffering of psoriatic patients.

Immune balancing: Some of the herbs are known also as immune balancing herbs—*Phylantus emblica, Azadirachta indica, Tinospora cordifolia*. So by using this herbal formula to cure psoriasis one will gain also a better immune system.

Prevention: after curing or at least ameliorating the symptoms, the herbs can be taken for a prolong time as a preventative composition for preventing recurrence of the disease as the plants have no known side effects.

DETAILED DESCRIPTION OF THE INVENTION

The present invention provides an oral composition for treating skin disorders comprising at least one herbal extract selected from the group consisting of *Azadirachta indica, Acacia catechu, Hemidesmus indicus, Tinospora cordofilia, Phyllanthus emblica, Terminalia bellirica* and *Terminalia chebula*.

The composition may comprise herbal extracts of at least five of the extracts selected from the group consisting of *Azadirachta indica, Acacia catechu, Hemidesmus indicus, Phyllanthus emblica, Terminalia bellirica* and *Terminalia chebula*.

The composition may comprise herbal extracts of *Azadirachta indica, Phyllanthus emblica, Terminalia bellirica* and *Terminalia chebula* and at least one other extract selected from *Acacia catechu* and *Hemidesmus indicus*.

The composition may comprise herbal extracts of *Azadirachta indica, Acacia catechu, Hemidesmus indicus Phyllanthus emblica, Terminalia bellirica* and *Terminalia chebula*.

The composition may comprise herbal extracts of *Azadirachta indica, Acacia catechu, Hemidesmus indicus, Phyllanthus emblica, Terminalia bellirica, Terminalia chebula* and *Tinospora cordofilia*.

The term "oral composition" refers to a composition adapted for oral administration.

The term "herbal extract" refers to an extract of an herb such as an aqueous extract, an alcoholic extract a water/alcohol extract of a selected herb.

The composition may further comprise an antacid. In some embodiments, the amount of antacid in the composition is 2 w/w %-30 w/w % out of the total weight of the composition. In some embodiments the antacid is selected from calcium carbonate, aluminum hydroxide and sodium bicarbonate.

The composition may be prepared in a form of a capsule in different sizes, e.g. between capsule size 000 to capsule size 4, and/or between a capsule of 60 mg weight of herbs' extracts in a capsule to 1700 mg weight of herbs' extracts in a capsule.

The composition may be prepared in a form of a tablet, pill, caplet, oral disintegrating tablet (ODT), pastille, lozenge, soft gel, lollipop, functional chewing gum, in different sizes with different concentrations of the ingredients.

The composition may also be prepared as a syrup, extended release syrups, syrup concentrate for dilution with and/or addition of carbonated water, juice or water, elixirs, decoctions, suspensions, solutions, emulsions, depositors, powders, sublingual drops, hot or cold infusions, herbal-tea, a tincture, a thin-film drug delivery (oral drug strip), a nasal spray, an oral spray, a transdermal gel, a transdermal patch, in different sizes with different concentrations of the ingredients.

The composition may be administrated orally, sublingually, buccally, sub-labial, rectally, or trans-dermally in different concentrations of the ingredients.

The compositions of the present invention optionally include other pharmaceutically acceptable artificial or natural materials, such as fillers, excipients, binders, disintegrants, glidants, lubricants, viscosity modifiers, diluents, surface active agents, such as surfactants, emulsifiers, foam modulators, pH modifying agents, abrasives, humectants, emollients, moisturizers, mouth feel agents, sweetening agents, flavor agents, colorants, preservatives, vehicles, and combinations thereof. It is understood that while general attributes of each of the above categories of materials may differ, there may be some common attributes and any given material may serve multiple purposes within two or more of such categories of materials.

The three components *Phyllanthus emblica*, *Terminalia bellirica* and *Terminalia chebula* constitute a known herbal traditional medicine by the name of "Triphala" which is known as a detoxifier. Without being limited to theory, the presence of Triphala in the composition assumingly accelerates removal of toxins from the digestion system, hence less toxins will reach the skin. The inventor of the invention found that Triphala is an important ingredient in treating psoriasis and skin diseases. Nonetheless, the composition according to the invention may also be prepared and successfully treat skin disorders such as psoriasis without Triphala.

It is noted that the traditional herbal composition Saribadyarista is not part of the scope of the present invention.

The composition of the invention may comprise pharmaceutical effective amounts of extracts of the following herbs used in Indian traditional medicine Ayurveda:
1. *Azadirachta indica*
2. *Acacia catechu* (sin. *Black catechu*)
3. *Hemidesmus indicus* R. Br.
4. *Phyllanthus emblica*
5. *Terminalia bellirica*
6. *Terminalia chebula*

In some embodiments the composition further comprises a pharmaceutical effective amount of an extract of *Tinospora cordifolia*.

The composition may utilize herbal dry extracts in the product. The term "herbal dry extract" relates herein to a solid preparation obtained by evaporating the solvent used in their production. The dry extract usually has a loss of weight on drying or water content of not more than 5% w/w. In some embodiments dry extracts of herbs are mixed together with other types of extracts of herbs.

The herbs in the composition can be used and mixed as simple powders or as any type of herbal extracts or a mixture of extracts type, such as simple extracts, standardized extracts, dry extracts, soft extracts, $CO_2$ extracts, aqueous extracts, organic solvents extracts, as macerated oils, essential oils, or as tinctures—alcoholic based or water based tinctures or both. The composition can use the extracts in any type of extract concentration e.g. 2:1, 5:1, 10:1 (the ratio of the weight of the plant before the extraction to the weight of the extracted matter) etc. Thus, it is contemplated that the amount of active compounds form each extract present in the composition may vary as would be appreciated by one of skill in the art.

The herbal extracts which are used in the composition of the invention can be purchased commercially or prepared according to any suitable extraction method known to one of skill in the art. The extracts may be prepared using water as the extracting solvent, water-alcohol solvent systems at various ratios, as well as other organic solvents such as alcohols (e.g. ethanol, methanol), chlorinated alkanes (e.g. dichloromethane, chloroform), alkanes (e.g. pentane, hexane, iso-octane), aromatic solvents (e.g. toluene). The extracts may be dried to obtain a dry extract by freeze drying or spray drying. Dry extracts are typically analytically analyzed to assure that no solvent has remained in the final extract. The dry extracts used in the examples presented herein below were purchased from Unicorn Natural Products Company (Private) LTD.

The composition may be prepared using specific concentrations for each of the herbs extract as follows:
1. *Azadirachta indica* 10:1
2. *Acacia catechu*, Black catechu 8:1
3. *Hemidesmus indicus* R. Br. 4:1
4. *Phyllanthus emblica* 10:1
5. *Terminalia bellirica* 4:1
6. *Terminalia chebula* 4:1
7. *Tinospora cordifolia* 4:1

The composition comprises a therapeutically effective amount of the herbs extracts present in the composition. "Therapeutically effective amount" means an amount of extract that, when administered to a subject for treating a skin disorder, is sufficient to effect such treatment (i.e. cure, ameliorate or improve severity of symptoms) for the skin disorder. The "therapeutically effective amount" will vary depending on the ratio between the extracts, disease state being treated, the severity or the disease treated, the age and relative health of the subject, the route and form of administration, the judgment of the attending medical practitioner, and other factors.

The mixture of extracts in the composition may comprise 0.5-97.5 W/W %, in some embodiments 10-90 W/W %, of each ingredient (*Azadirachta indica, Acacia catechu, Hemidesmus indicus* R. Br., *Phyllanthus emblica, Terminalia bellirica,* and *Terminalia chebula* out of the total weight of the mixture of herbal extracts. In some embodiments the mixture of herbal extracts may further comprise 0.5-50 W/W % *Tinospora cordifolia*.

The mixture of extracts may constitute between 1 to 100 W/W %, in some embodiments between 10 to 97.5 W/W %, in some embodiments between 10 to 30 W/W %, out of the total weight of the composition.

The composition may comprise the following weight percentages of each ingredient out of the total weight of the plant extracts in the composition: 1-90 W/W % *Azadirachta indica,* 1-90 W/W % *Acacia catechu,* 1-90 W/W % *Hemidesmus indicus* R. Br., 0.1-20 W/W % *Phyllanthus emblica,* 0.1-20 W/W % *Terminalia bellirica,* 0.1-20 W/W % *Terminalia chebula,* and optionally 1-90 W/W % *Tinospora cordifolia* out of the total weight of the dry composition.

The composition may comprise the following weight percentages of each ingredient out of the total weight of the plant extracts in the composition: 10-60 W/W % *Azadirachta indica,* 10-60 W/W % *Acacia catechu,* 10-60 W/W % *Hemidesmus indicus* R. Br., 1-10 W/W % *Phyllanthus emblica,* 1-10 W/W % *Terminalia bellirica,* 1-10 W/W % *Terminalia chebula* and 0-85 W/W % *Tinospora cordifolia*.

In some embodiments weight percentages of each ingredient out of the total weight of the plant extracts in the composition is as follows: 20-50 W/W % *Azadirachta indica,* 20-50 W/W % *Acacia catechu,* 20-50 W/W % *Hemidesmus indicus* R. Br., 2-8 W/W % *Phyllanthus emblica,* 2-8 W/W % *Terminalia bellirica,* and 2-8 W/W % *Terminalia chebula* and 0-40 W/W % *Tinospora cordifolia*.

In some embodiments weight percentages of each ingredient out of the total weight of the active ingredients in the composition is as follows: 20-40 W/W % *Azadirachta indica,* 20-40 W/W % *Acacia catechu,* 20-40 W/W % *Hemidesmus indicus* R. Br., 3-7 W/W % *Phyllanthus emblica,* 3-7 W/W % *Terminalia bellirica,* 3-7 W/W % *Terminalia chebula* and 0-25 W/W % *Tinospora cordifolia*.

In some embodiments weight percentages of each ingredient out of the total weight of the active ingredients in the composition is as follows: 20-40 W/W % *Azadirachta indica,* 20-40 W/W % *Acacia catechu,* 20-40 W/W % *Hemidesmus indicus* R. Br., 3-7 W/W % *Phyllanthus emblica,* 3-7 W/W % *Terminalia bellirica,* 3-7 W/W % *Terminalia chebula* and 3-25 W/W % *Tinospora cordifolia*.

In some embodiments the weight percentage of *Azadirachta indica* out of the total weight of the active ingredients in the composition is 0.5 W/W %, 0.7 W/W %, 1 W/W %, 1.5 W/W %, 2 W/W %, 3 W/W %, 4 W/W %, 5 W/W %, 6 W/W %, 7 W/W %, 8 W/W %, 9 W/W %, 10 W/W %, 11 W/W %, 12 W/W %, 13 W/W %, 14 W/W %, 15 W/W %, 16 W/W %, 17 W/W %, 18 W/W %, 19 W/W %, 20 W/W %, 21 W/W %, 22 W/W %, 23 W/W %, 24 W/W %, 25 W/W %, 26 W/W %, 27 W/W %, 28 W/W %, 29 W/W %, 30 W/W %, 31 W/W %, 32 W/W %, 33 W/W %, 34 W/W %, 35 W/W %, 36 W/W %, 37 W/W %, 38 W/W %, 39 W/W %, 40 W/W %, 41 W/W %, 42 W/W %, 43 W/W %, 44 W/W %, 45 W/W %, 46 W/W %, 47 W/W %, 48 W/W %, 49 W/W %, 50 W/W %, 51 W/W %, 52 W/W %, 53 W/W %, 54 W/W %, 55 W/W %, 56 W/W %, 57 W/W %, 58 W/W %, 59 W/W %, 60 W/W %, 61 W/W %, 62 W/W %, 63 W/W %, 64 W/W %, 65 W/W %, 66 W/W %, 67 W/W %, 68 W/W %, 69 W/W %, 70 W/W %, 71 W/W %, 72 W/W %, 73 W/W %, 74 W/W %, 75 W/W %, 76 W/W %, 77 W/W %, 78 W/W %, 79 W/W %, 80 W/W %, 81 W/W %, 82 W/W %, 83 W/W %, 84 W/W %, 85 W/W %, 86 W/W %, 87 W/W %, 88 W/W %, 89 W/W % or 90 W/W %.

In some embodiments the weight percentage of *Acacia catechu* out of the total weight of the active ingredients in the composition is 0.5 W/W %, 0.7 W/W %, 1 W/W %, 1.5 W/W %, 2 W/W %, 3 W/W %, 4 W/W %, 5 W/W %, 6 W/W %, 7 W/W %, 8 W/W %, 9 W/W %, 10 W/W %, 11 W/W %, 12 W/W %, 13 W/W %, 14 W/W %, 15 W/W %, 16 W/W %, 17 W/W %, 18 W/W %, 19 W/W %, 20 W/W %, 21 W/W %, 22 W/W %, 23 W/W %, 24 W/W %, 25 W/W %, 26 W/W %, 27 W/W %, 28 W/W %, 29 W/W %, 30 W/W %, 31 W/W %, 32 W/W %, 33 W/W %, 34 W/W %, 35 W/W %, 36 W/W %, 37 W/W %, 38 W/W %, 39 W/W %, 40 W/W %, 41 W/W %, 42 W/W %, 43 W/W %, 44 W/W %, 45 W/W %, 46 W/W %, 47 W/W %, 48 W/W %, 49 W/W %, 50 W/W %, 51 W/W %, 52 W/W %, 53 W/W %, 54 W/W %, 55 W/W %, 56 W/W %, 57 W/W %, 58 W/W %, 59 W/W %, 60 W/W %, 61 W/W %, 62 W/W %, 63 W/W %, 64 W/W %, 65 W/W %, 66 W/W %, 67 W/W %, 68 W/W %, 69 W/W %, 70 W/W %, 71 W/W %, 72 W/W %, 73 W/W %, 74 W/W %, 75 W/W %, 76 W/W %, 77 W/W %, 78 W/W %, 79 W/W %, 80 W/W %, 81 W/W %, 82 W/W %, 83 W/W %, 84 W/W %, 85 W/W %, 86 W/W %, 87 W/W %, 88 W/W %, 89 W/W % or 90 W/W %.

In some embodiments the weight percentage of *Hemidesmus indicus* out of the total weight of the active ingredients in the composition is 0.5 W/W %, 0.7 W/W %, 1 W/W %, 1.5 W/W %, 2 W/W %, 3 W/W %, 4 W/W %, 5 W/W %, 6 W/W %, 7 W/W %, 8 W/W %, 9 W/W %, 10 W/W %, 11 W/W %, 12 W/W %, 13 W/W %, 14 W/W %, 15 W/W %, 16 W/W %, 17 W/W %, 18 W/W %, 19 W/W %, 20 W/W %, 21 W/W %, 22 W/W %, 23 W/W %, 24 W/W %, 25 W/W %, 26 W/W %, 27 W/W %, 28 W/W %, 29 W/W %, 30 W/W %, 31 W/W %, 32 W/W %, 33 W/W %, 34 W/W %, 35 W/W %, 36 W/W %, 37 W/W %, 38 W/W %, 39 W/W %, 40 W/W %, 41 W/W %, 42 W/W %, 43 W/W %, 44 W/W %, 45 W/W %, 46 W/W %, 47 W/W %, 48 W/W %, 49 W/W %, 50 W/W %, 51 W/W %, 52 W/W %, 53 W/W %, 54 W/W %, 55 W/W %, 56 W/W %, 57 W/W %, 58 W/W %, 59 W/W %, 60 W/W %, 61 W/W %, 62 W/W %, 63 W/W %, 64 W/W %, 65 W/W %, 66 W/W %, 67 W/W %, 68 W/W %, 69 W/W %, 70 W/W %, 71 W/W %, 72 W/W %, 73 W/W %, 74 W/W %, 75 W/W %, 76 W/W %, 77 W/W %, 78 W/W %, 79 W/W %, 80 W/W %, 81 W/W %, 82 W/W %, 83 W/W %, 84 W/W %, 85 W/W %, 86 W/W %, 87 W/W %, 88 W/W %, 89 W/W % or 90 W/W %.

In some embodiments the weight percentage of *Phyllanthus emblica* out of the total weight of the active ingredients in the composition is 0.5 W/W %, 0.7 W/W %, 1 W/W %, 1.5 W/W %, 2 W/W %, 3 W/W %, 4 W/W %, 5 W/W %, 6 W/W %, 7 W/W %, 8 W/W %, 9 W/W %, 10 W/W %, 11 W/W %, 12 W/W %, 13 W/W %, 14 W/W %, 15 W/W %, 16 W/W %, 17 W/W %, 18 W/W %, 19 W/W %, 20 W/W %, 21 W/W %, 22 W/W %, 23 W/W %, 24 W/W %, 25 W/W %, 26 W/W %, 27 W/W %, 28 W/W %, 29 W/W %, 30 W/W %, 31 W/W %, 32 W/W %, 33 W/W %, 34 W/W %, 35 W/W %, 36 W/W %, 37 W/W %, 38 W/W %, 39 W/W %, 40 W/W %, 41 W/W %, 42 W/W %, 43 W/W %, 44 W/W %, 45 W/W %, 46 W/W %, 47 W/W %, 48 W/W %, 49 W/W %, 50 W/W %, 51 W/W %, 52 W/W %, 53 W/W %, 54 W/W %, 55 W/W %, 56 W/W %, 57 W/W %, 58 W/W %, 59 W/W %, 60 W/W %, 61 W/W %, 62 W/W %, 63 W/W %, 64 W/W %, 65 W/W %, 66 W/W %, 67 W/W %, 68 W/W %, 69 W/W %, 70 W/W %, 71 W/W %, 72 W/W %, 73 W/W %, 74 W/W %, 75 W/W %, 76 W/W %, 77 W/W %, 78 W/W %, 79 W/W %, 80 W/W %, 81 W/W %, 82 W/W %, 83 W/W %, 84 W/W %, 85 W/W %, 86 W/W %, 87 W/W %, 88 W/W %, 89 W/W % or 90 W/W %.

In some embodiments the weight percentage of *Terminalia bellirica* out of the total weight of the active ingredients in the composition is 0.5 W/W %, 0.7 W/W %, 1 W/W %, 1.5 W/W %, 2 W/W %, 3 W/W %, 4 W/W %, 5 W/W %, 6 W/W %, 7 W/W %, 8 W/W %, 9 W/W %, 10 W/W %, 11 W/W %, 12 W/W %, 13 W/W %, 14 W/W %, 15 W/W %, 16 W/W %, 17 W/W %, 18 W/W %, 19 W/W %, 20 W/W %, 21 W/W %, 22 W/W %, 23 W/W %, 24 W/W %, 25 W/W %, 26 W/W %, 27 W/W %, 28 W/W %, 29 W/W %, 30 W/W %, 31 W/W %, 32 W/W %, 33 W/W %, 34 W/W %, 35 W/W %, 36 W/W %, 37 W/W %, 38 W/W %, 39 W/W %, 40 W/W %, 41 W/W %, 42 W/W %, 43 W/W %, 44 W/W %, 45 W/W %, 46 W/W %, 47 W/W %, 48 W/W %, 49 W/W %, 50 W/W %, 51 W/W %, 52 W/W %, 53 W/W %, 54 W/W %, 55 W/W %, 56 W/W %, 57 W/W %, 58 W/W %, 59 W/W %, 60 W/W %, 61 W/W %, 62 W/W %, 63 W/W %, 64 W/W %, 65 W/W %, 66 W/W %, 67 W/W %, 68 W/W %, 69 W/W %, 70 W/W %, 71 W/W %, 72 W/W %, 73 W/W %, 74 W/W %, 75 W/W %, 76 W/W %, 77 W/W %, 78 W/W %, 79 W/W %, 80 W/W %, 81 W/W %, 82 W/W %, 83 W/W %, 84 W/W %, 85 W/W %, 86 W/W %, 87 W/W %, 88 W/W %, 89 W/W % or 90 W/W %.

In some embodiments the weight percentage of *Terminalia chebula* out of the total weight of the active ingredients in the composition is 0.5 W/W %, 0.7 W/W %, 1 W/W %, 1.5 W/W %, 2 W/W %, 3 W/W %, 4 W/W %, 5 W/W %, 6 W/W %, 7 W/W %, 8 W/W %, 9 W/W %, 10 W/W %, 11 W/W %, 12 W/W %, 13 W/W %, 14 W/W %, 15 W/W %, 16 W/W %, 17 W/W %, 18 W/W %, 19 W/W %, 20 W/W %, 21 W/W %, 22 W/W %, 23 W/W %, 24 W/W %, 25 W/W %, 26 W/W %, 27 W/W %, 28 W/W %, 29 W/W %, 30 W/W %, 31 W/W %, 32 W/W %, 33 W/W %, 34 W/W %, 35 W/W %, 36 W/W %, 37 W/W %, 38 W/W %, 39 W/W %, 40 W/W %, 41 W/W %, 42 W/W %, 43 W/W %, 44 W/W %, 45 W/W %, 46 W/W %, 47 W/W %, 48 W/W %, 49 W/W %, 50 W/W %, 51 W/W %, 52 W/W %, 53 W/W %, 54 W/W %, 55 W/W %, 56 W/W %, 57 W/W %, 58 W/W %, 59 W/W %, 60 W/W %, 61 W/W %, 62 W/W %, 63 W/W %, 64 W/W %, 65 W/W %, 66 W/W %, 67 W/W %, 68 W/W %, 69 W/W %, 70 W/W %, 71 W/W %, 72 W/W %, 73 W/W %, 74 W/W %, 75 W/W %, 76 W/W %, 77 W/W %, 78 W/W %, 79 W/W %, 80 W/W %, 81 W/W %, 82 W/W %, 83 W/W %, 84 W/W %, 85 W/W %, 86 W/W %, 87 W/W %, 88 W/W %, 89 W/W % or 90 W/W %.

In some embodiments the weight percentage of *Tinospora cordifolia* out of the total weight of the active ingredients in the composition is 0.5 W/W %, 0.7 W/W %, 1 W/W %, 1.5 W/W %, 2 W/W %, 3 W/W %, 4 W/W %, 5 W/W %, 6 W/W %, 7 W/W %, 8 W/W %, 9 W/W %, 10 W/W %, 11 W/W %, 12 W/W %, 13 W/W %, 14 W/W %, 15 W/W %, 16 W/W %, 17 W/W %, 18 W/W %, 19 W/W %, 20 W/W %, 21 W/W %, 22 W/W %, 23 W/W %, 24 W/W %, 25 W/W %, 26 W/W %, 27 W/W %, 28 W/W %, 29 W/W %, 30 W/W %, 31 W/W %, 32 W/W %, 33 W/W %, 34 W/W %, 35 W/W %, 36 W/W %, 37 W/W %, 38 W/W %, 39 W/W %, 40 W/W %, 41 W/W %, 42 W/W %, 43 W/W %, 44 W/W %, 45 W/W %, 46 W/W %, 47 W/W %, 48 W/W %, 49 W/W %, 50 W/W %, 51 W/W %, 52 W/W %, 53 W/W %, 54 W/W %, 55 W/W %, 56 W/W %, 57 W/W %, 58 W/W %, 59 W/W %, 60 W/W %, 61 W/W %, 62 W/W %, 63 W/W %, 64 W/W %, 65 W/W %, 66 W/W %, 67 W/W %, 68 W/W %, 69 W/W %, 70 W/W %, 71 W/W %, 72 W/W %, 73 W/W %, 74 W/W %, 75 W/W %, 76 W/W %, 77 W/W %, 78 W/W %, 79 W/W %, 80 W/W %, 81 W/W %, 82 W/W %, 83 W/W %, 84 W/W %, 85 W/W %, 86 W/W %, 87 W/W %, 88 W/W %, 89 W/W % or 90 W/W %.

The composition may comprises 3-18 W/W % Triphala out of the total weight of the composition comprising equal parts of *Phyllanthus emblica, Terminalia bellirica*, and *Terminalia chebula*.

The composition may comprises 3 W/W %, 4 W/W %, 5 W/W %, 6 W/W %, 7 W/W %, 8 W/W %, 9 W/W %, 10 W/W %, 11 W/W %, 12 W/W %, 13 W/W %, 14 W/W %, 15 W/W %, 16 W/W %, 17 W/W % or 18 W/W % Triphala out of the total weight of the composition comprising equal parts of *Phyllanthus emblica, Terminalia bellirica*, and *Terminalia chebula*

The formula may further comprise anti-adherent and lubricant agent—e.g. magnesium stearate, and an anti-caking agent e.g. silicon dioxide.

The herbal formula may further comprise any other excipient or additives such as—calcium stearate, sodium stearate, talc, corn starch, Arabic gum, and maltodextrins, silicon oil, colloidal silica, DL-leucine, sodium lauryl sulfate, silaceous material like colloidal silica i.e. Syloid®, pyrogenic silica, hydrated sodium silioaluminate, any hydrogenated vegetable oil such as Sterotex®, waxes, Stear-O-Wet™, glyceryl behenate such as Compritol®, liquid paraffin, boric acid, sodium benzoate, sodium oleate, sodium acetate, magnesium lauyil sulfate. In some embodiments, the formula comprises magnesium stearate in an amount of 3% by total weight of the composition.

The formula further comprises an anti-caking agent. In some embodiments the anti-caking agent is silicon dioxide. In some embodiments the formula comprise silicon dioxide in an amount of 3% by total weight of the composition.

The oral composition of the invention is efficient and naturally derived. Nonetheless, additional synthetic anti-inflammatory, antifungal, antibacterial, and/or antioxidant active ingredients may be also included in the oral composition. The addition of these active ingredients should be evaluated as to not to react with or detract from the efficacy and bioavailability of the composition of the plant extracts.

By way of example the oral composition can be prepared according to the following example: the powder mixture of herbs and the optional additives were mixed by a V-Blender and encapsulated by a fully automatic BOSCH® capsule filling machine. In some embodiments the mixture is encapsulated in an edible vegetarian capsule such as hydroxypropyl methylcellulose (HPMC). It may also be encapsulated in other types of capsules such as—soft gelatin capsules, hard gelatin capsules, fish gelatin capsules, starch capsules, pullulan capsules, polyvinyl acetate (PVA) capsules, liquid-filled hard capsules (LFHC), soft gelatin capsules (SGC). They may be also enteric coated capsules, sustained release capsules, or rectal capsules.

Use of the Composition in Treating Skin Disorders

The composition of the invention is used for treating skin disorders including psoriasis, psoriatic arthritis, acne, aphthous stomatitis, gingivitis, pemphigus vulgaris, urticaria, dermatitis including seborrheic dermatitis, atopic dermatitis, dermatoses and eczema. The composition can be administered in a dose of mixture of herbal extracts ranging from 50 mg to 3000 mg between one to 3 times per day, and in some embodiments every 1, 2, 3, 4, 5, 6, 7 or 8 hours.

In some embodiments the composition can be administered in a dose of mixture of herbal extracts ranging from 50 mg to 2500 mg between one to 3 times per day, and in some embodiments every 1, 2, 3, 4, 5, 6, 7 or 8 hours.

In some embodiments the composition can be administered in a dose of mixture of herbal extracts ranging from 50 mg to 2000 mg between one to 3 times per day, and in some embodiments every 1, 2, 3, 4, 5, 6, 7 or 8 hours.

In some embodiments the composition can be administered in a dose of mixture of herbal extracts ranging from 50 mg to 1700 mg between one to 3 times per day, and in some embodiments every 1, 2, 3, 4, 5, 6, 7 or 8 hours.

In some embodiment the composition is administered as a tincture in a dose range of between 5 to 30 drops once to three times a day, and in some embodiments every 1, 2, 3, 4, 5, 6, 7 or 8 hours.

In some embodiment the method of treating a skin disorder (e.g. psoriasis) comprises administering the composition of the invention in an amount of dose of mixture of herbal extracts to body weight ration ranging between 0.70 mg/Kg to 24 mg/Kg. In some embodiment the method of treating a skin disorder (e.g. psoriasis) comprises administering the composition in an amount of dose to body weight ration ranging between 5 mg/Kg to 20 mg/Kg. In some embodiment the method of treating a skin disorder (e.g. psoriasis) comprises administering the composition in an amount of dose of mixture of herbal extracts to body weight ration of 1 mg/Kg, 2 mg/Kg, 3 mg/Kg, 4 mg/Kg, 5 mg/Kg, 6 mg/Kg, 7 mg/Kg, 8 mg/Kg, 9 mg/Kg, 10 mg/Kg, 11 mg/Kg, 12 mg/Kg, 13 mg/Kg, 14 mg/Kg, 15 mg/Kg, 16 mg/Kg, 17 mg/Kg, 18 mg/Kg, 19 mg/Kg, 20 mg/Kg, 21 mg/Kg, 22 mg/Kg, 23 mg/Kg and 24 mg/Kg.

In some embodiments the composition of the invention is administered to a patient in need between once to three times a day. In some embodiments the composition is administered to a patient in need every other day. In some embodiments the composition is administered to a patient in order to prevent the appearance of a skin disorder (e.g. psoriasis). In some embodiments the composition is administered to a patient in order to avoid recurrence of a skin disorder (e.g. psoriasis).

In some embodiments the oral composition of the invention is administered for a period of between 2 to 26 weeks, 2 to 16 weeks or 2 to 12 weeks. In some embodiments the oral composition is administered for a period of between 3 to 10 weeks. In some embodiments the oral composition is administered for a period of 4 to 6 weeks. In some embodiments the composition of the invention is administered until the patient feels a relief in the symptoms of the skin disorder. In some embodiments the oral composition is administered to the patient for a period of time after a relief in the symptoms is observed and/or reported by the patient, to reduce the possible recurrence of the symptoms. In some embodiments the oral composition is administered to the patient indefinitely or for at least 2, 3 or 4 weeks after a relief in the symptoms is observed and/or reported by the patient, to reduce the possible recurrence of the symptoms.

All the above dosage amounts refer to amount of herbal extracts in the composition. The concentrations of the herbal extracts in the total weight of the composition may vary depending on the form of the composition, in particular on the amount of additives and excipients which are added to the composition. The person versed in the art would know who how? to adapt the dosage accordingly.

As stated above, the composition of the invention makes use of naturally derived extracts of the aforementioned plants. It is noted however, that complete or partial removal of an active ingredient, or several active ingredients (i.e. compounds which are otherwise found in the extracts) from the aforementioned extracts, is still within the scope of the present invention. Also, replacement of an active ingredient or several active ingredients with a synthetic equivalent would still be considered part of the scope of the present invention.

In some embodiments an average improvement of about 85% in the severity of the symptoms can be observed.

Possible Mode of Action

Psoriasis disease involves several causes that influence the patient. A weak digestion system that does not digest the food properly, leads to accumulation of toxins in the body. The toxins that are produced as byproducts by the digestion system are absorbed into the blood system, pass through the liver and reach the skin through the blood system. It is assumed that these toxins have a crucial contribution to psoriasis outbreak and severity.

Without being bound to theory, it is hypothesized that the surprising therapeutic properties of the composition of the invention may be explained by the versatility of its components in treating several factors which contribute to the persistence of the disease. To begin with, the use of Triphala, namely the combination of *Phyllanthus emblica*, *Terminalia bellirica* and *Terminalia chebula*, which prevents the production of impurities in the intestine, has a significant amplifying impact on the effect of the other ingredients of the formula. *Phyllanthus emblica* also has a liver boosting effect. These herbs are combined with two other liver boosting herbs, namely—*Azadirachta indica*, and *Tinospora cordifolia*. The liver boosting herbs, increase the activity of the liver, which further reduces the amount of toxins which are present in the blood system and reach the skin. This reduction in the amount of toxins reaching the infected area boosts the direct therapeutic activity of the herbs *Azadirachta indica*, *Acacia catechu* and *Hemidesmus indicus* on the skin disease. The composition of the invention also reduces the inflammatory component of psoriasis by the combined action of *Azadirachta indica*, *Phyllanthus emblica*, *Hemidesmus indicus* and *Tinospora cordifolia*.

An alternative or parallel possible mode of action which may account for the effectiveness of the composition of the invention, is that *Phyllanthus emblica*, *Tinospora cordifolia*, *Hemidesmus indicus*, and *Azadirachta indica* each have "a cooling effect" which attenuates the "heat element" in the stomach, means it reduces the heating influence of the gastric enzymes—Hydrochloric acid and Pepsinogen, and increase the low pH in the stomach, and consequently also reduces the inflammatory component of the disease.

Another possible mode of action is that *Emblica officinalis*, *Tinospora cordifolia*, *Azadirachta indica*, *Hemidesmus indicus*, *Acacia catechu*, *Terminalia bellirica* and *Terminalia chebula* have been shown to possess antioxidant and anti-inflammatory activities, and activities in reduction of cell damage and protective activities against DNA damage.

A balancing effect of *Phylantus emblica*, *Azadirachta indica* and *Tinospora cordifolia* on the immune system may also attribute to the positive effect of the composition on possible autoimmune etiology of the breakout of the disease.

The composition of the invention can be administered as a food additive. The invention thus further provides a food additive comprising the composition of the invention.

The composition can be included in a variety of products such as a nutraceutical, a dietary supplement and a medicament.

The invention further provides a nutraceutical comprising the composition of the invention.

The invention further provides a dietary supplement comprising the composition of the invention.

The invention further provides a medicament comprising the composition of the invention.

According to another aspect the invention provides a kit which includes a product comprising the composition of the invention and instructions for administration of the product according to the method for treating a skin disorder according to the invention as described above.

EXAMPLES

The following Examples further illustrate the present invention, but it is understood that the invention is not limited thereto.

Example 1

Dry herb extracts, in the weight ratios listed in Table 1 were mixed to obtain a homogeneous powder. 400 mg of homogeneous powder was encapsulated in vegetarian HPMC according to common techniques known in the art.

TABLE 1

Composition ingredients (For a 400 Veg HPMC capsule)

| Botanical name of the herb | Extract conc. | Traditional (Sanskrit) name of the herb | % Herb in the formula | Herb extract amount in the capsule (mg) |
|---|---|---|---|---|
| *Azadirachta indica* | 10:1 | Neem | 44 | 165.44 |
| *Acacia catechu*, Black catechu | 8:1 | Khadira | 24 | 90.24 |
| *Hemidesmus indicus* R. Br. | 4:1 | Sariva | 20 | 75.2 |
| *Phyllanthus emblica* | 10:1 | Amalaki | 4 | 15.04 |
| *Terminalia bellirica* | 4:1 | Bibhitaki | 4 | 15.04 |
| *Terminalia chebula* | 4:1 | Haritaki | 4 | 15.04 |
| Subtotal | | | 100 | 376 |
| Magnesium stearate | | — | 3 | 12 |
| Silicon dioxide | | — | 3 | 12 |
| Total | | | — | 400 |

Example 2

Pilot Studies

The pilot formula of Example 1 was used for conducting a pilot study in which nine patients were treated for three months by oral administration of the formula.

The patients suffered from various degrees of psoriasis. They were randomly selected by the order of arrival to the clinic. Some of the patients also suffered from other diseases—diabetes, high blood pressure, heart diseases and more.

The patients were administered two capsules (2×400 mg) in the evening and two capsules (2×400 mg) in the morning (daily dose of 1,600 mg) for 8 weeks. All patient were administered the doses on an empty stomach. During the whole experiment there were no other psoriasis medications administered to the patients.

A comparison of the condition of the patients before, during treatment (every 3 to 4 weeks) and after treatment was conducted by questioning the patients, examining the patients, and observations of the spreading, color, and thickness of the lesions.

The collected data was classified and analyzed by the commonly used of the psoriasis studies methodology.

The patients reported no side-effects, and no complaints.

To evaluate the effectiveness of the treatment The PASI index described below was used.

PASI—Psoriasis Area and Severity Index

PASI is an index of the severity of psoriasis and its spreading. This is an acceptable index at clinical experiments of the psoriasis disease. The PASI has to be analyzed before, during, and after the treatment in order rely on it. A low PASI means an insignificant level of disease whereas a high PASI means a severe one.

Not all the PASI are similar, and in clinical experiments it is acceptable to use a "Modified PASI" to fit to the researchers needs. The studies related to the present invention use a generic PASI in an unmodified form as explained below.

Skin section: The body of each patient was divided to—4 sections.

Each section was classified separately and afterwards all sections were summarized together according to a predetermined weight for each section: LEGS—40% of the entire body, BODY TRUNK—Belly, Chest, back—30%; ARMS—20%; and HEAD and NECK—10%.

Coverage Area: The coverage percent of infected skin in each area is estimated and converged to ranked according to a conversion table as presented in Table 2:

TABLE 2

Conversion of infected skin coverage and coverage rank

| Coverage percent | Coverage rank |
| --- | --- |
| 0% | 0 |
| <10% | 1 |
| 10-29% | 2 |
| 30-49% | 3 |
| 50-69% | 4 |
| 70-89% | 5 |
| 90-100% | 6 |

For example, if the head is about 40% ("about" is to be construed as ±5%) covered by infected skin, the rank for the head will be 3.

Severity: The severity of the psoriasis is measured by 4 distinct parameters: Itching (1), Erythema (E), Scaling (S) and Thickness (T).

The term "Erythema" refers to redness of the skin caused by dilatation and congestion of the capillaries. The term "Scaling" refers to the loss of the outer layer of the epidermis layer of the skin (the outer layer of the 3 layers of the skin) in large, scale-like flakes. The skin appears dry and cracked. Scaling skin is also called: desquamation, dropping of scales, flaking skin, peeling skin, scaly skin. The term "Thickness" is defined as the skin elevation comparing to surrounding normal skin.

Each one of the 4 distinct parameters are measured in each section separately. They are measured on a 0-4 scale as detailed in Table 3.

TABLE 3

Conversion of severity of parameters to PASI score.

| Severity | Score |
| --- | --- |
| None | 0 |
| Some | 1 |
| Moderate | 2 |
| Sever | 3 |
| Maximum | 4 |

For example, if the patient complained about a medium degree of itching from the psoriasis lesions in the head section, then the itching index for the head (I Head) was given a score value 2.

If the area was slightly erythematic then the erythema index for the head (E Head) was given a score value of 1.

Additionally the scaling of the head (S head) and thickness of the lesions in the head (T head) had to be to be evaluated as well as all 4 parameters I, E, S, T for all three parts of the skin.

Index summary: After determining all 20 classifications of above, the 5 severity scores for each one of the four body parts was summarized, and multiplied by score of coverage area and by with the weight percentage of that body section as follows:

HEAD:($I$ head+$E$ head+$S$ head+$T$ head)×$A$ head× 0.1=TOTAL head

ARMS:($I$ arms+$E$ arms+$S$ arms+$T$ arms)×$A$ arms× 0.2=TOTAL arms

BODY:($I$ body+$E$ body+$S$ body+$T$ body)×$A$ body× 0.3=TOTAL body

LEGS:($I$ legs+$E$ legs+$S$ legs+$T$ legs)×$A$ legs× 0.4=TOTAL legs

To summarize, PASI=TOTAL head+TOTAL arms+TOTAL body+TOTAL legs. The PASI values range from zero (0—no Psoriasis) to 96 (covers the entire body with maximum itching, erythema, scaling and thickness). The PASI results are summarized in Table 4.

TABLE 4

| Patient Number | PASI Before Treatment | PASI End of Treatment | Change (%) |
| --- | --- | --- | --- |
| 1 | 15.3 | 8.1 | 47 |
| 2 | 62 | 52 | 16.1 |
| 3 | 13.9 | 11.7 | 15.8 |
| 4 | 9.2 | 4.2 | 54.3 |
| 5 | 4.4 | 2.8 | 36.4 |
| 6 | 6 | 2.8 | 53.3 |
| 7 | 5.1 | 1.6 | 68.6 |
| 8 | 4 | 1.2 | 70 |
| 9 | 2.4 | 1.6 | 33.3 |
| Average change in PASI | | | 43.9% |

The results presented above demonstrate PASI improvement for all the patients that participated in the pilot study and an average change of 43.9%, which is considered to be as an excellent result in psoriasis treatments, indicate that the treatment is effective for treating psoriasis with a natural, non-side effects, herbal remedy. All patients exhibited PASI improvement even after the first follow up which took place after 3-4 weeks.

Core Ingredients

The composition of the mixture of herbal extracts in the tested composition is presented in Table 5.

TABLE 5

| Botanical name | W/W % in the composition (*) |
|---|---|
| Azadirachta indica | 44 |
| Acacia catechu, Black catechu | 24 |
| Hemidesmus indicus R. Br. | 20 |
| Phyllanthus emblica | 4 |
| Terminalia bellirica | 4 |
| Terminalia chebula | 4 |

It is noted that some of the patients also exhibited improvement in other co-existing dermal conditions such as Acne, Seborrheic dermatitis and one case of Pemphigus. Therefore, the formula can be used to treat not only psoriasis but also other skin diseases and related problems such as: psoriasis, psoriatic arthritis, acne, aphthous stomatitis, gingivitis, pemphigus vulgaris, urticaria, dermatitis including seborrheic dermatitis, atopic dermatitis, dermatoses and eczema and for detoxifying treatments. This can be demonstrated by conducting corresponding experiments on patients suffering from these other disorders.

Example 3

An oral composition of herbal extracts according to another example embodiment of the invention is presented in Table 6 (extract concentrations are as given in Example 1).

TABLE 6

| Botanical name | W/W % in the composition (*) |
|---|---|
| Azadirachta indica | 24 |
| Acacia catechu, Black catechu | 44 |
| Hemidesmus indicus R. Br. | 20 |
| Phyllanthus emblica | 4 |
| Terminalia bellirica | 4 |
| Terminalia chebula | 4 |

Example 4

An oral composition of herbal extracts according to another example embodiment of the invention is presented in Table 7 (extract concentrations are as given in Example 1).

TABLE 7

| Botanical name | W/W % in the composition (*) |
|---|---|
| Azadirachta indica | 48 |
| Hemidesmus indicus R. Br. | 40 |
| Phyllanthus emblica | 4 |
| Terminalia bellirica | 4 |
| Terminalia chebula | 4 |

Example 5

An oral composition of herbal extracts according to another example embodiment of the invention is presented in Table 8 (extract concentrations are as given in Example 1).

TABLE 8

| Botanical name | W/W % in the composition (*) |
|---|---|
| Azadirachta indica | 48 |
| Acacia catechu, Black catechu | 40 |
| Phyllanthus emblica | 4 |
| Terminalia bellirica | 4 |
| Terminalia chebula | 4 |

Example 6

An oral composition of herbal extracts according to another example embodiment of the invention is presented in Table 9 (extract concentrations are as given in Example 1).

TABLE 9

| Botanical name | W/W % in the composition (*) |
|---|---|
| Tinospora cordifolia | 48 |
| Acacia catechu, Black catechu | 40 |
| Phyllanthus emblica | 4 |
| Terminalia bellirica | 4 |
| Terminalia chebula | 4 |

Example 7

An oral composition of herbal extracts according to another example embodiment of the invention is presented in Table 10 (extract concentrations are as given in Example 1).

TABLE 10

| Botanical name | W/W % in the composition (*) |
|---|---|
| Tinospora cordifoilia | 48 |
| Hemidesmus indicus R. Br. | 40 |
| Phyllanthus emblica | 4 |
| Terminalia bellirica | 4 |
| Terminalia chebula | 4 |

Example 8

An oral composition of herbal extracts according to another example embodiment of the invention is presented in Table 11 (extract concentrations are as given in Example 1).

TABLE 11

| Botanical name | W/W % in the composition (*) |
|---|---|
| Tinospora cordifolia | 85 |
| Phyllanthus emblica | 5 |

TABLE 11-continued

| Botanical name | W/W % in the composition (*) |
|---|---|
| *Terminalia bellirica* | 5 |
| *Terminalia chebula* | 5 |

Example 9

An oral composition of herbal extracts according to another example embodiment of the invention is presented in Table 12 (extract concentrations are as given in Example 1).

TABLE 12

| Botanical name | W/W % in the composition (*) |
|---|---|
| *Azadirachta indica* | 85 |
| *Phyllanthus emblica* | 5 |
| *Terminalia bellirica* | 5 |
| *Terminalia chebula* | 5 |

Example 10

An oral composition of herbal extracts according to another example embodiment of the invention is presented in Table 13 (extract concentrations are as given in Example 1).

TABLE 13

| Botanical name | W/W % in the composition (*) |
|---|---|
| *Acacia catechu, Black catechu* | 85 |
| *Phyllanthus emblica* | 5 |
| *Terminalia bellirica* | 5 |
| *Terminalia chebula* | 5 |

Example 11

An oral composition of herbal extracts according to another example embodiment of the invention is presented in Table 14 (extract concentrations are as given in Example 1).

TABLE 14

| Botanical name | W/W % in the composition (*) |
|---|---|
| *Hemidesmus indicus R. Br.* | 85 |
| *Phyllanthus emblica* | 5 |
| *Terminalia bellirica* | 5 |
| *Terminalia chebula* | 5 |

Example 12

An oral composition of herbal extracts according to another example embodiment of the invention is presented in Table 15 (extract concentrations are as given in Example 1).

TABLE 15

| Botanical name | W/W % in the composition (*) |
|---|---|
| *Azadirachta indica* | 50 |
| *Acacia catechu, Black catechu* | 25 |
| *Hemidesmus indicus R. Br.* | 25 |

Example 13

An oral composition of herbal extracts according to another example embodiment of the invention is presented in Table 16 (extract concentrations are as given in Example 1).

TABLE 16

| Botanical name | W/W % in the composition (*) |
|---|---|
| *Azadirachta indica* | 60 |
| *Tinospora cordifolia* | 20 |
| Acacia catechu, Black catechu | 20 |

Example 14

An oral composition of herbal extracts according to another example embodiment of the invention is presented in Table 17 (extract concentrations are as given in Example 1).

TABLE 17

| Botanical name | W/W % in the composition (*) |
|---|---|
| *Azadirachta indica* | 60 |
| *Hemidesmus indicus R. Br.* | 20 |
| *Tinospora cordifolia* | 20 |

Example 15

An oral composition of herbal extracts according to another example embodiment of the invention is presented in Table 17 (extract concentrations are as given in Example 1).

TABLE 17

| Botanical name | W/W % in the composition (*) |
|---|---|
| *Azadirachta indica* | 55 |
| *Acacia catechu, Black catechu* | 15 |
| *Hemidesmus indicus R. Br.* | 15 |
| *Tinospora cordifolia* | 15 |

Example 16

An oral composition of herbal extracts according to another example embodiment of the invention is presented in Table 18 (extract concentrations are as given in Example 1).

TABLE 16

| Botanical name | W/W % in the composition (*) |
| --- | --- |
| *Tinospora cordifolia* | 44 |
| *Acacia catechu, Black catechu* | 24 |
| *Hemidesmus indicus* R. Br. | 20 |
| *Phyllanthus emblica* | 4 |
| *Terminalia bellirica* | 4 |
| *Terminalia chebula* | 4 |

Example 17

An oral composition of herbal extracts according to another example embodiment of the invention is presented in Table 19 (extract concentrations are as given in Example 1).

TABLE 19

| Botanical name | W/W % in the composition (*) |
| --- | --- |
| *Acacia catechu, Black catechu* | 44 |
| *Azadirachta indica* | 24 |
| *Hemidesmus indicus* R. Br. | 20 |
| *Phyllanthus emblica* | 4 |
| *Terminalia bellirica* | 4 |
| *Terminalia chebula* | 4 |

(*) All the above ingredients in all the compositions we mentioned may appear in the dry extract concentrations: of between 1:1 to 50:1.

Example 18

Each one of the compositions presented in Examples 3 to 17, as well as others within the specified concentration ranges discussed above, can be tested for efficacy according to the protocol detailed in Example 2 for the composition of Example 1 by orally administering the composition to a group of patients following a given dosage regimen. The dosage regimen can follow the dosage regimen described in Example 2 or be modified for optimization. The condition of the patients before, during and after treatment can be performed by questioning and examining the patients, making observations on the lesions and determining the PASI index in a similar manner as detailed above accordingly, and collecting reports from the patients regarding side effects.

Additionally or alternatively the efficacy of the administration of the compositions according to the invention can be tested by:
  collecting quality-of-life (QOL) questionnaires from the patients during the course treatment. To this end, the combination of two questionnaires—the Skindex-29 with the generic SF-36 can be used.
  Self administered PASI (SAPASI) in which the patients may evaluate the PASI by themselves.
  Immunology tests, wherein the frequency of CLA+CD8+ T cells in the blood of psoriasis patients is monitored during the course of treatment as it correlates closely with the severity of the disease.
  Objective assessment of psoriasis lesion thickness for PASI scoring using 3D digital imaging. The 3D skin surface images are obtained using a laser scanner.

Example 19

A 500 mg composition of the present invention having the w/w % as defined in Table 1 and formulated into capsules is tested on a group of 40 to 50 patients suffering from psoriasis that are administered with the composition for six months. The patients commit not to use other herbal medicine in addition to the composition of the invention. The ingredients of the composition is brought to the attention of the patients so they can confirm that they are not allergic to any of the ingredients. The patients commit to inform of any side effect or reaction to the administration of the composition.

The patients arrive to a clinic for an interview with a practitioner and receive the composition. The interview includes gathering of information regarding the severity of the itching of the lesions, disease history, past and present treatment (at the time of the interview), nails and joints condition, and personal information such as age, occupation, marital status. The patients make once in 6 weeks follow-up visits. In each visit the practitioner interviews the patient and fills a questionnaire to define the severity of the lesions. The questionnaire is based on common PASI questionnaires in psoriasis research. The practitioner also makes photos of the lesions for documentation and comparison. The patients are administered with two capsules of 500 mg each twice a day that can be taken in parallel to any other type of treatment for treating psoriasis.

An average reduction of above 50% in the PASI degree of the patients is considered a successful experiment that demonstrate the effectiveness of the medicament and treatment.

The invention claimed is:

1. A composition for treating skin disorders comprising a mixture of herbal extracts of *Azadirachta indica, Acacia Catechu, Hemidesmus indicus, Phyllanthus emblica, Terminalia bellirica* and *Terminalia chebula* wherein said composition comprising 1-90 W/W % *Azadirachta indica*, 1-90 W/W % *Acacia catechu*, 1-90 W/W % *Hemidesmus indicus* R. Br., 0.1-20 W/W % *Phyllanthus emblica*, 0.1-20 W/W % *Terminalia bellirica* and 0.1-20 W/W % *Terminalia chebula*, and optionally further comprising 1-90 W/W % *Tinospora cordifolia* out of the total weight of a dry composition.

2. The composition according to claim 1, further comprising *Tinospora cordifolia*.

3. The composition according to claim 1, comprising 24-48 W/W % *Azadirachta indica*, 24-44 W/W % *Acacia catechu*, 20-44 W/W % *Hemidesmus indicus* R. Br., 4-5 W/W % *Phyllanthus emblica*, 4-5 W/W % *Terminalia bellirica* and 4-5 W/W % *Terminalia chebula*, and optionally further comprising 15-85 W/W % *Tinospora cordifolia* out of the total weight of a dry composition.

4. The composition according to claim 1, further comprising an antacid.

5. The composition according to claim 1, further comprising a pharmaceutically accepted carrier.

6. The composition according to claim 1, for treating a skin disorder selected from:
  psoriasis, psoriatic arthritis, acne, aphthous stomatitis, gingivitis, pemphigus vulgaris, urticaria, dermatitis selected from seborrheic dermatitis and atopic dermatitis, dermatoses and eczema.

7. The composition according to claim 1, wherein the composition is for treating psoriasis.

8. The composition according to claim 1, for use in detoxifying treatments.

9. The composition according to claim 1, wherein the composition is formulated in the form of a capsule, a suspension, a tablet, a chewable tablet, a lozenge, syrup, paste, mouth spray or a nose spray.

10. The composition according to claim 1, wherein the composition is an oral composition.

11. The composition according to claim 1, wherein the composition is for use in at least one of a nutraceutical, a dietary supplement and a medicament for treating a skin disorder.

12. A kit comprising a product comprising a composition as defined in claim 1, and instructions for administering the composition.

13. A method for treating a skin disorder comprising administering the composition defined in claim 1 to a patient in need thereof.

14. The method according to claim 13, wherein the skin disorder is selected from:
psoriasis, psoriatic arthritis, acne, aphthous stomatitis, gingivitis, pemphigus vulgaris, urticaria, dermatitis selected from seborrheic dermatitis and atopic dermatitis, dermatoses and eczema.

15. The method according to claim 13, wherein the skin disorder is psoriasis.

16. The method according to claim 13, comprising at least one of
Orally, sublingually, buccally, sub-labial, rectally, or trans-dermally administering a composition of claim 1;
administering an oral dose of a composition of claim 1;
administering between once to four times a day an oral dose of one or two capsules comprising a composition of claim 1;
administering an oral dose of two capsules comprising 400 mg to 500 mg of a composition of claim 1 between once to three times a day;
administering between 0.70 mg/kg or 24 mg/kg of an oral composition of claim 1;
administering a composition of claim 1 for a period of 2 weeks to half a year, and
administering a composition of claim 1 for a period of 3 to 4 weeks.

* * * * *